US012405197B2

(12) United States Patent
Zettel et al.

(10) Patent No.: US 12,405,197 B2
(45) Date of Patent: Sep. 2, 2025

(54) METHOD FOR EVALUATION OF CHEMICAL RESISTANCE OF THERMOPLASTICS

(71) Applicant: Healthcare Surfaces Summit, Stevensville, MT (US)

(72) Inventors: Mike Zettel, Bloomfield, MD (US); Yubiao Liu, Johnson City, TN (US); James Hicks, Atlanta, GA (US); Kay Bernhard, Darmstadt (DE); Pooja Bajaj, Fairfield, CT (US); Mark Lamont, Port Jefferson, NY (US); Ellen Turner, Kingsport, TN (US)

(73) Assignee: Healthcare Surfaces Summit, Stevensville, MT (US)

( * ) Notice: Subject to any disclaimer, the term of this patent is extended or adjusted under 35 U.S.C. 154(b) by 309 days.

(21) Appl. No.: 18/135,420

(22) Filed: Apr. 17, 2023

(65) Prior Publication Data
US 2023/0341306 A1    Oct. 26, 2023

Related U.S. Application Data

(60) Provisional application No. 63/332,270, filed on Apr. 18, 2022.

(51) Int. Cl.
*G01N 3/303* (2006.01)
*G01N 3/04* (2006.01)
*G01N 33/44* (2006.01)

(52) U.S. Cl.
CPC ............. *G01N 3/303* (2013.01); *G01N 3/04* (2013.01); *G01N 33/442* (2013.01);
(Continued)

(58) Field of Classification Search
CPC ............ G01N 3/303; G01N 3/04; G01N 3/08; G01N 3/30; G01N 33/442;
(Continued)

(56) References Cited

FOREIGN PATENT DOCUMENTS

CN    117129347 A  *  11/2023

OTHER PUBLICATIONS

Knustsoffe International, Maintaining Clarity Long-Term, Chemical and Environmental Stress-Crack Resistance of PMMA-Based Compounds in the Medical Environment. Munich, May 2019.
Tech Briefs Media Group, Standard Test Method for Evaluation of Chemical Resistance of Thermoplastics for Non-Disposable Medical Devices—A Voice from Industry Collaboration Through the COVID-19 Pandemic (Oct. 1, 2022).
ASTM International, ASTM D638-14 Standard Test Method for Tensile Properties of Plastics, 1996.
ASTM International, ASTM D6110-18 Standard Test Method for Determining the Charpy Impact Resistance of Notched Specimens of Plastics, 1996.
(Continued)

*Primary Examiner* — Jonathan M Dunlap
(74) *Attorney, Agent, or Firm* — Sierra IP Law, PC; Mark D. Miller

(57) ABSTRACT

The present invention provides a standard testing methodology for making quantitative determinations as to the chemical resistance of thermoplastics commonly used for non-disposable medical devices by evaluating the retention of tensile and/or impact properties of the thermoplastic materials after exposure to chemicals associated with healthcare grade disinfectants. Versions of the test methods may be used with any of a variety of different thermoplastic materials, each having a different stiffness or elastic modulus; and versions of the test methods may be used with any of a variety of different hospital grade cleaning agents or disinfectants. Using the methodology of embodiments of the present invention, different thermoplastic materials may be tested against different cleaners or disinfectants to provide a uniform basis for comparison. This allows those who make chemicals, polymers and medical equipment to have a uniform way of evaluating those materials for compatibility with various cleaners and disinfectants used in the medical industry to make objective comparisons, and to allow end users to make the same evaluations and comparisons.

18 Claims, 7 Drawing Sheets

(52) U.S. Cl.
CPC ............... *G01N 2203/001* (2013.01); *G01N 2203/0039* (2013.01); *G01N 2203/024* (2013.01); *G01N 2203/0252* (2013.01); *G01N 2203/0264* (2013.01); *G01N 2203/0476* (2013.01)

(58) Field of Classification Search
CPC ..... G01N 2203/0039; G01N 2203/001; G01N 2203/0476; G01N 2203/0264; G01N 2203/024; G01N 2203/0252; G01N 2203/0017; G01N 2203/0098; G01N 2203/0282; G01N 2203/0298
See application file for complete search history.

(56) References Cited

OTHER PUBLICATIONS

ASTM International, ASTM D543-21 Standard Practices for Evaluating the Resistance of Plastics to Chemical Reagents, 1996.
ASTM International, ASTM D618-21 Standard Practices for Conditioning Plastics for Testing, 1996.
ASTM International, ASTM D883-22 Standard Terminology Relating to Plastics, 1996.
ASTM International, ASTM D6110-04 Standard Test Methods for Determining the Charpy Impact Resistance of Notched Specimens of Plastics, 1996.

* cited by examiner

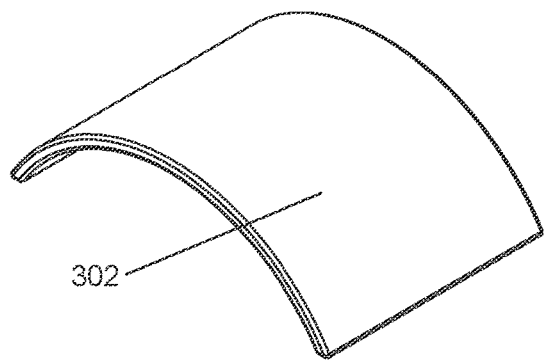 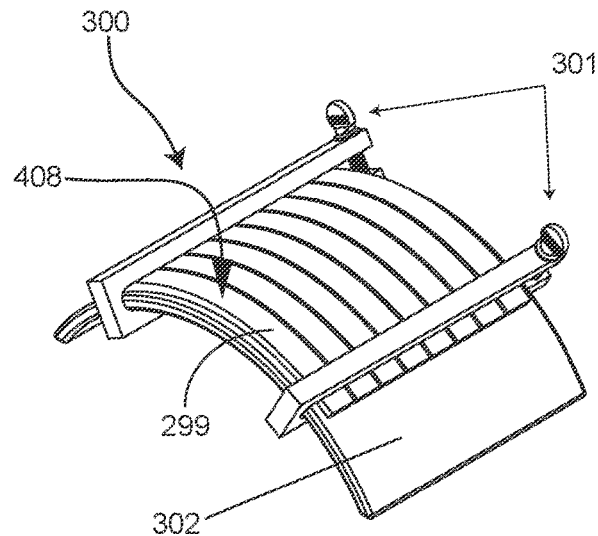
Figure 3A                          Figure 3B
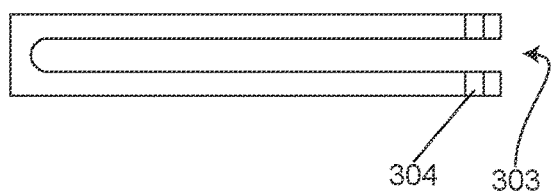 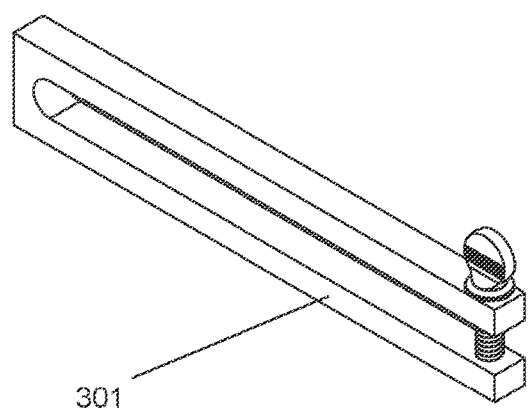
Figure 3C                          Figure 3D

US 12,405,197 B2

METHOD FOR EVALUATION OF CHEMICAL RESISTANCE OF THERMOPLASTICS

PRIORITY CLAIM

This application claims the benefit of U.S. provisional application Ser. No. 63/332,270 filed on Apr. 18, 2022.

FIELD OF THE INVENTION

The present invention relates to methods for testing the effect of cleaning or disinfecting chemicals on the materials making up the surfaces of medical devices and facilities, and more particularly to providing standard method for the evaluation of chemical resistance of thermoplastics for non-disposable medical devices.

BACKGROUND OF THE INVENTION

Patients and health care workers are constantly exposed to microbes that cause deadly infections. Despite the best efforts of healthcare professionals to effectively clean and disinfect devices and facilities, healthcare acquired infections (HAI's) continue to be one of the top causes of death behind heart disease, cancer and COVID 19. One reason for this is the incompatibility between certain chemical cleaning or disinfecting materials and the surfaces they are used to clean or disinfect. In some situations, disinfecting a surface made of a particular material using an incompatible disinfectant may damage the surface, resulting in the creation of cracks or gaps in the surface, which provide places where germs and pathogens may accumulate putting patients at risk of potentially contracting infections. As new and existing thermoplastic materials are built into the surfaces of medical devices or surfaces, it is important to know which cleaning or disinfecting materials may be used on those surfaces without causing unacceptable degradation which may affect patient care. As a result, there is a need to determine which surface materials and textiles can be effectively cleaned and disinfected using standard and EPA hospital grade disinfectants without damaging surfaces and products used in the built environment.

SUMMARY OF THE INVENTION

The present invention provides a standard testing methodology for making quantitative determinations as to the chemical resistance of thermoplastics commonly used for non-disposable medical devices by evaluating the retention of tensile and/or impact properties of the thermoplastic materials after exposure to chemicals associated with healthcare grade disinfectants. Versions of the test methods may be used with any of a variety of different thermoplastic materials, each having a different stiffness or elastic modulus; and versions of the test methods may be used with any of a variety of different hospital grade cleaning agents or disinfectants. Using the methodology of embodiments of the present invention, different thermoplastic materials may be tested against different cleaners or disinfectants to provide a uniform basis for comparison. This allows those who make chemicals, polymers and medical equipment to have a uniform way of evaluating those materials for compatibility with various cleaners and disinfectants used in the medical industry to make objective comparisons, and to allow end users to make the same evaluations and comparisons.

The methods of the present invention are intended to be only a part of a broader and more comprehensive evaluation of surface materials and chemicals, and are not intended as the sole selection criteria for any particular material or chemical, nor are they intended to constitute any type of certification or guarantee of any particular outcomes.

In embodiments of the invention, a thermoplastic material intended for potential use on a surface of a medical device or facility is selected for evaluation, and a proposed chemical (e.g., a disinfectant) is selected for compatibility. A plurality of test specimens and a plurality of control specimens of the thermoplastic material are obtained, the specimens having a uniform size and shape. An elasticity modulus is determined for the material, which may be low (flexible), medium (less flexible) or high (more rigid). Based on the elasticity modulus of the material, a semi-cylindrical straining jig is selected having a curvature that is related to the modulus. In embodiments of the invention, the radius of a jig for materials having a lower modulus will be smaller than the radius of a jig used for materials having a higher modulus; that is, the curvature of the exterior cylindrical wall a jig used with testing a flexible thermoplastic material will be more severe (more rounded) than the (flatter) curvature of the exterior wall of a jig used with testing a more rigid thermoplastic material.

In embodiments of the invention, the test specimens are temporarily attached along the exterior cylindrical wall of the jig in a way that does not damage the specimens themselves. In some embodiments, clamps may be used at opposite ends of the test specimens to hold them against the jig. This temporary attachment bends the thermoplastic material in conformity with the curvature of the jig, inducing stress or strain on the material. The selected chemical is then brought into contact with the exposed exterior surfaces of the test specimens on the jig. In embodiments of the invention, this may be accomplished by saturating a non-woven fabric with the selected chemical, and placing the soaked fabric on the test specimens. Depending upon the test being performed and the elasticity modulus of the material being tested, the period of exposure may be from about 24 hours to about 7 days. The fabric may be periodically soaked during this time to account for evaporation.

After the exposure time has passed, the test specimens are removed from the jig and may be tested for tensile strength and/or impact strength. Tensile testing has no orientation requirements. However, for impact testing, each test specimen should be mounted vertically on a pendulum apparatus such that the plane of the specimen has an orientation that is perpendicular to the plane of the base of the pendulum apparatus (with the longitudinal bottom edge of the specimen resting on the base), and the surface of the test specimen that was in contact with the chemical should be facing away from the striking head of the apparatus. The test specimens are then tested in the apparatus by causing the head to strike the test specimen, and recording the results. The control specimens are also tested in the same way. If the results of the test specimens are satisfactory, for example the test samples come in at a threshold of greater than ninety percent (90%) of the results of the control specimen, then the test specimen may be considered not to have been significantly affected by the chemical, and may be considered compatible with that chemical. However, if the test samples come in below the threshold, then the material may not be considered compatible with the chemical. So long as the same methodology and threshold is followed for all test materials, use of the methods of the present invention may provide a standard by which all thermoplastic materials may be compared against common cleaners and disinfectants.

In some aspects, the methods comprise testing an thermoplastic material for compatibility with a chemical comprising the steps of selecting an thermoplastic material to be tested, selecting a chemical for testing with the selected thermoplastic material, determining a modulus of the thermoplastic material, selecting a geometry for specimens of the thermoplastic material including a thickness (which may be, for example and without limitation, according to the dimensions defined for ASTM D 638 Type 1 tensile bars), selecting a jig having a radius of curvature based on the thickness of the specimens and a strain based on the modulus of the thermoplastic material, placing a plurality of test specimens on the jig, placing a plurality of control specimens on the jig (for example and without limitation, the plurality of test specimens and the plurality of control specimens should be at least five specimens of each), exposing outer surfaces of the test specimens to the selected chemical for a first predetermined period of time (which may be, for example and without limitation, between about 24 hours and about 7 days), but not exposing the control specimens to the chemical, removing both the test specimens and the control specimens from the jig, and waiting for a second predetermined period of time (which may be, for example about one hour), performing impact testing on both the test specimens and the control specimens and recording the results, averaging the impact results of the test specimens, averaging the impact results of the control specimens, and comparing the average test impact results with the average control impact results. In some aspects, the comparison may show that the average test results were greater than ninety percent (90%) of the average control results.

In some aspects the testing of each of the test specimens may include: placing the test specimen upon an impact pendulum such that a plane defined by the specimen has an orientation that is perpendicular to a plane defined by a base of the pendulum with the exposed outer surface of the specimen facing away from a pendulum head, and striking the test specimen with the pendulum head to obtain an impact result; and the testing of each of the control specimens may include: placing the control specimen upon an impact pendulum such that a plane defined by the specimen has an orientation that is perpendicular to a plane defined by a base of the pendulum, and striking the control specimen with a pendulum head to obtain an impact result. Such impact testing may or may not be followed by tensile testing.

In some aspects, after waiting the second period of time, the methods may include testing each test specimen for tensile properties and recording the tensile results, testing each control specimen for tensile properties and recording the tensile results, averaging the tensile results of the test specimens, averaging the tensile results of the control specimens, and comparing the average test tensile results with the average control tensile results. Such tensile testing may or may not be followed by impact testing.

In some aspects, the radius of curvature for the jig is based on the following formula where "t" is the thickness of the material, "Σ" is the strain, and "R" is the radius:

$$R = \frac{\left(\frac{1}{\Sigma} - 1\right)t}{2}$$

In some aspects, instead of or in addition to impact testing, the methods may include additional steps of testing each test specimen and testing each control specimen for tensile properties (which may be, for example and without limitation, according to ASTM D 638) recording the tensile results, averaging the tensile results of the test specimens, averaging the tensile results of the control specimens, and comparing the average test tensile results with the average control tensile results. In some aspects, the comparison may show that the average test results were greater than ninety percent (90%) of the average control results.

It is therefore an object of the present invention to provide methods for evaluating the compatibility of thermoplastic materials used on the surfaces of medical devices or facilities with chemicals used for cleaning and disinfecting those surface materials.

It is also an object of the present invention to provide a uniform method of comparing the compatibility of different thermoplastic materials with different chemicals used for cleaning and disinfecting the surfaces of medical devices and facilities.

The above-described objects, advantages and features of the invention, together with the organization and manner of operation thereof, will become apparent from the following detailed description when taken in conjunction with the accompanying drawings, wherein like elements have like numerals throughout the several drawings described herein. Further objects, benefits and other advantages of the present invention will become readily apparent from the detailed description of the preferred embodiments.

BRIEF DESCRIPTION OF THE DRAWINGS

FIG. 3A is a perspective view of an embodiment of a strain jig of the present invention.

FIG. 3B is a perspective view of an embodiment of a strain jig of the present invention having a plurality of test samples mounted thereon.

FIG. 3C is a side view of an exemplary clamp of an embodiment of the invention.

FIG. 3D is a perspective view of an exemplary clamp of an embodiment of the invention.

DETAILED DESCRIPTION

Figure 1:
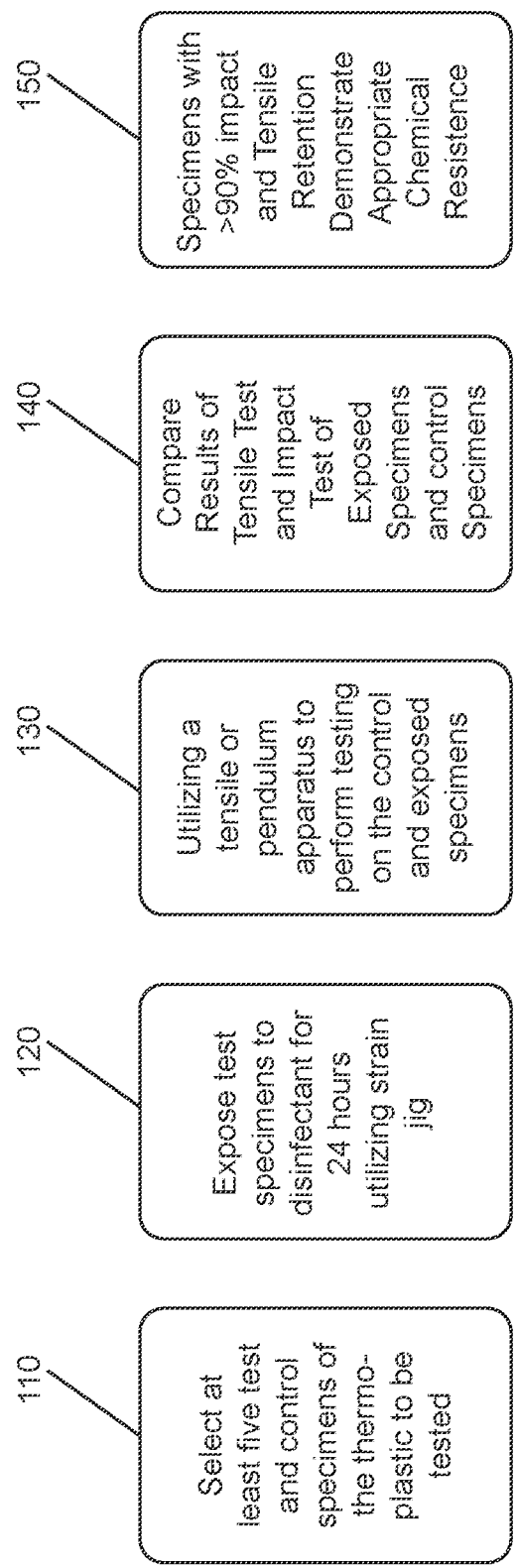
FIG. 1 shows an embodiment of a method of evaluating chemical resistance of thermoplastics.

It is to be appreciated that the methods described herein do not purport to address or resolve any safety concerns associated with their use. It is the responsibility of the user of the methods disclosed herein to establish appropriate safety and health practices and determine the applicability of regulatory limitations prior to use.

In the Background, Summary, and Drawings descriptions above, in the Detailed Description and the claims below, and in the accompanying drawings, reference is made to particular features of the invention. It is to be understood that the disclosure of the invention in this specification does not necessarily include all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. may optionally be present.

Where reference is made herein to a method comprising two or more defined steps, the defined steps can be carried out in any order or simultaneously unless otherwise specified, and the method can include one or more other steps which are carried out before any of the defined steps, between two of the defined steps, or after all the defined steps unless otherwise specified.

Definitions

Non-woven fabric. As used in this application, non-woven fabric refers to a fabric made from fibers which are held together by physical or chemical means excluding weaving, knitting or paper making.

Strain jig. As used in this application, a strain jig refers to a tool used to place test specimens under appropriate strain.

Saturation. As used in this application, saturation refers to the state or process that occurs when no more of something can be absorbed, combined with, or added.

Quaternary Ammonium Compound (QAC). As used in this application QAC refers to any salt derived from ammonium in which attached to the nitrogen are four alkyl or aryl substituents, each substituent is not necessarily equal in molecular weight to the other.

Reusable. As used in this application, reusable describes any medical equipment and/or device that health care providers can reuse on multiple patients, and may include devices that typically do not come into direct patient contact or by normal use only contact unbroken skin. Examples would be but not limited to bedside monitoring equipment, drug delivery pumps or handheld probes or sensors.

The present invention is related to methods for determining the chemical resistance of thermoplastic materials. Multiple embodiments of the invention are described hereinafter with reference to the accompanying drawings. This invention may, however, be embodied in many different forms and should not be construed as limited to the embodiments set forth herein; rather, these embodiments are provided so that this disclosure will be thorough and complete and will fully convey the scope of the invention to those skilled in the art.

Reference will now be made in detail to certain embodiments of the invention, examples of which are illustrated in the accompanying drawings. While the invention will be described in reference to these embodiments, it will be understood that they are not intended to limit the invention. To the contrary, the invention is intended to cover alternatives, modifications, and equivalents that are included within the spirit and scope of the invention, including different combinations of the features identified herein. In the following disclosure, specific details are given to provide a thorough understanding of the invention. However, it will be apparent to one skilled in the art that the present invention may be practiced without all of the specific details provided.

In some embodiments, a strain jig 300 is used to expose test specimens 299 to chemicals. According to some embodiments, as illustrated in FIGS. 3A-3D, a strain jig 300 is a provided in the form of a semi-cylindrical fixture having an outer surface 302 with a radius of curvature, such that when a flat plastic specimen 299 is placed on the jig surface 302, an inner surface 404 of the specimen 299 is in direct contact with the jig surface 302, and an outer surface 408 of the specimen 299 is not in contact with the jig. Bending of the flat plastic specimen 299 on the jig in this way will impart the desired strain level. According to some embodiments, the strain jig 300 may include two retention mechanisms 301 to secure opposite ends of the specimen(s) 299 to the curved outer surface of the jig. In an example embodiment shown in FIGS. 3C an 3D, this retention mechanism 301 comprises a U-shaped device with a tapped hole 303 through a first portion of the mechanism and a drill hole 304 through another portion of the mechanism. The retention mechanisms 301 should be designed such that they retain but do not damage the specimens 299. The illustrated embodiment shows eight specimens, although any suitable number of specimens may be used for a given test, depending upon the size of the jig and the dimensions of the specimens.

In embodiments of the methods of the present invention, uniform specimen dimensions should be used. According to some methods, specimen geometry may conform to the dimensions defined for ASTM D 638 Type 1 tensile bars. Although this standard (ASTM D 638) is used in the descriptions of certain embodiments the invention herein, other standard dimensions may be used. It is to be appreciated in order to obtain appropriate comparisons of the effect of chemicals on different thermoplastic materials, the same (uniform) dimension geometry should be used for all materials tested using the methods disclosed herein. Among other things, the thickness ("t") of the material is determined by the standard selected. For ASTM D 638 Type 1, the thickness of the material is one-eighth inch (1/8") (i.e., 0.125 in).

Once a thermoplastic material and sample dimensions are selected for testing, its published properties should be obtained. These properties include the elasticity modulus for the material which may be expressed in KSI=kilo pounds per square inch, or GPa=gigapascals. The modulus will help classify the material into one of three different broad categories of stiffness: low (more flexible), medium (less flexible) and high (more rigid). These three categories are shown in Table 1 below, which reflects how the modulus level (KSI or GPa) is used to determine the high and low amount of strain that the material may be expected to endure without failure. A strain level ("Σ") may then be selected from the table.

TABLE 1

Prescribed Strain Levels for Selected Modulus Ranges

| Modulus (of material being evaluated) | Low <435 KSI <3 GPa | Medium 435 KSI-600 KSI 3 GPa-4.13 GPa | High >600 KSI >4.13 GPa |
|---|---|---|---|
| High Strain | 1.5% | 1.0% | 0.3% |
| Low Strain | 0.75% | 0.5% | 0.15% |

Once the material thickness ("t") and the strain level ("Σ") are determined, a jig 300 having an appropriate radius and curvature may then be selected. In most embodiments, the design of the strain jig 300 is based on the following known relationship between strain and radius of curvature:

$$\sum = \frac{1}{\frac{2R}{t}+1} \quad R = \frac{\left(\frac{1}{\Sigma}-1\right)t}{2}$$

Where "Σ" is the strain; "R" is the semi-cylinder radius of curvature; and "t" is the thickness of the test sample. The illustrated embodiment of FIG. 3E reflects a jig having a strain of 1.5%, resulting in an internal radius of 3.938 and an outer radius of 4.19 (see Table 2 below).

By way of example and without limitation, a set of exemplary jig dimensions are set forth in Table 2 below. This table reflects the radius of a jig using the equation above, a thickness "t" of ⅛" (0.125 inches), and the strains found in Table 1 above ranging from 0.15% through 1.5%. The thickness of the jig itself is 0.25" (as reflected in FIG. 3E), providing a radius number for the inner and outer surfaces of the jig.

TABLE 2

| Test Jig | Strain level for an ASTM 0.125 in thick specimen | | | | | |
|---|---|---|---|---|---|---|
| Dimensions | 0.15% | 0.30% | 0.50% | 0.75% | 1.00% | 1.50% |
| Outer Radius (in) | 41.67 | 20.87 | 12.48 | 8.39 | 6.28 | 4.19 |
| Thickness (in) | 0.25 | 0.25 | 0.25 | 0.25 | 0.25 | 0.25 |
| Inner Radius (in) | 41.42 | 20.62 | 12.23 | 8.14 | 6.03 | 3.94 |

Figure 2:
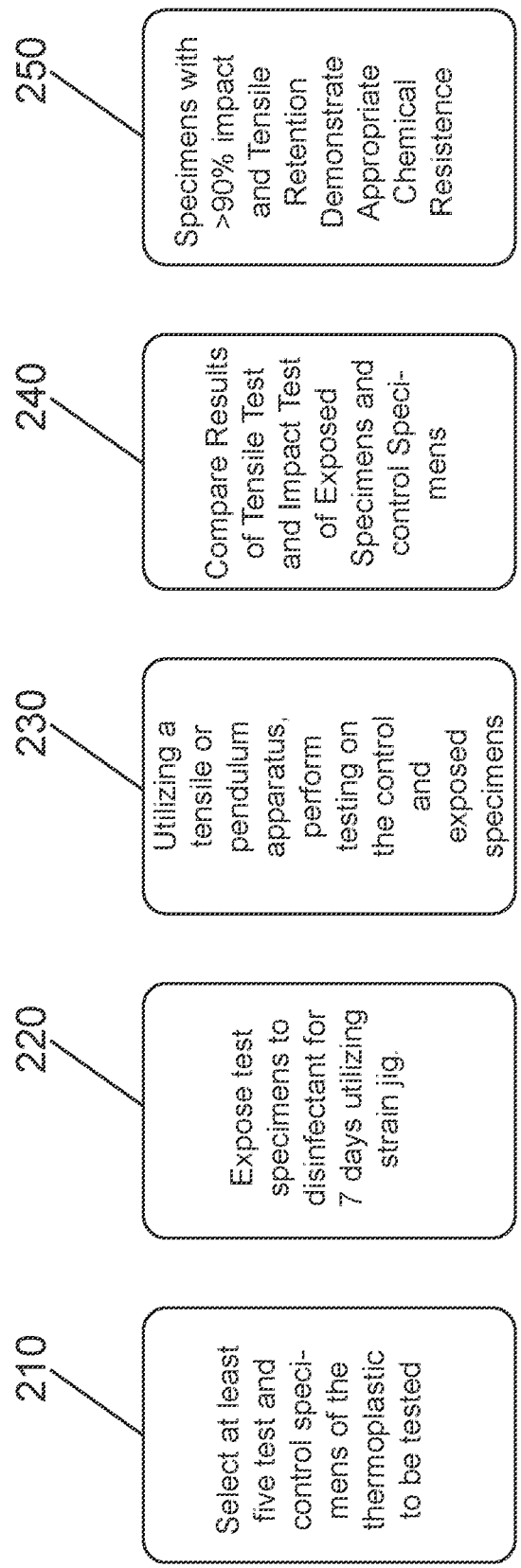
FIG. 2 shows an alternative embodiment of a method of evaluating chemical resistance of thermoplastics.
Figure 3E:
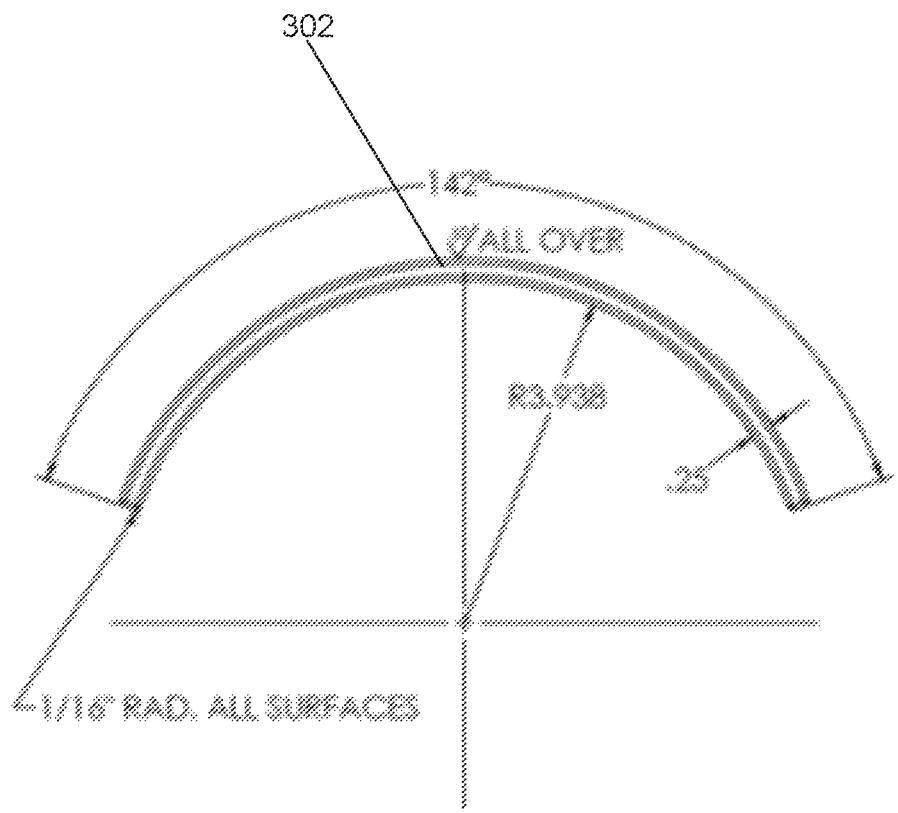
FIG. 3E shows a schematic view of dimensions of an embodiment of a jig of the present invention.

A set of basic steps of a test method of some embodiments of the present invention are referred to in FIGS. 1 and 2. Referring to the first steps 110, 210 of these embodiments, the test specimens are exposed to chemicals associated with healthcare grade disinfectants at room temperature. According to some embodiments, these test specimens can be tensile bar specimens. According to some embodiments, these test specimens can be flexural bar specimens. In some embodiments the tests may be conducted in the standard laboratory atmosphere of 23±2° C. [73±3.6° F.] and 50±10% relative humidity. In some embodiments there may be other appropriate temperatures depending on the material or customers end-use specifications. In some embodiments, the specimens will be deflected to impart the specified strain corresponding to the materials modulus (See Table 1).

According to FIGS. 1 and 2, referring to some methods, a minimum of five test specimens and five control 110, 210 specimens are recommended for all test sets. Specimens, test and control, should be marked to indicate orientation and exposure surface. According to some methods, referring to FIGS. 1, 2 and 3, tensile specimens may be placed in the strain jig 300 such that the gauge section width, nominally 13 mm (0.51 inches), is flush with the strain jig 300 curvature ensuring requisite strain is achieved. The control and test specimens may be placed on the same jig, or on separate identical jigs. The specimens should be secured at opposite ends of the jig(s) such that the securing mechanisms impart negligible interference with the intended test section.

In some embodiments, the specimens should be secured next to each other at opposite ends with the push pin side facing down toward the strain jig 300. Here, push pin refers to a surface marking that occurs due to the process of making the specimens via injection molding. The push pin marks can create a defect that could interfere with the testing when the chemical is applied. For accurate testing, it is a recommended that those pin marks be against the surface of the jig and away from the chemical exposure.

According to the embodiments of FIGS. 1 and 2, the specimens may be exposed at high strain for about 24 hours 120, and/or a low strain for about seven days 220. In most embodiments, the control specimens should undergo the same deflection for the same period of time as the test specimens, but without exposure to chemicals. According to some methods, once the required time of either about 24 hours or about seven days has elapsed, the test specimens (exposed and control) are removed from the strain jig 300 and allowed to relax for a minimum of about one hour. In some embodiments, test specimens should be tested within about 24 hours after removal from strain jig 300. Tensile properties of specimens may then be evaluated according to standard tensile testing methodology (Reference ASTM D 638). Impact properties may be evaluated according to a modified unnotched impact testing methodology (Reference ASTM D 6110).

Both tensile and/or impact testing may be performed. The applicability of either test will ordinarily depend upon the intended function of the material being tested. For example, if the material needs to be strong in order to support significant weight, then tensile testing may be more important and should be performed. On the other hand, if the material may be subject to dropping (such as a medical device), or to having items dropped on it (such as a floor or counter top), then impact testing may be more important and should be performed. In some situations, both tensile and impact testing may be important, and so both tests should be performed.

Referring to steps 120 and 220 of FIGS. 1 and 2, a nonwoven material may be placed over each test specimen. In some embodiments, the nonwoven material may be, for example, nominally 13 mm in width and 50 mm in length. In these methods, the nonwoven material may be saturated with the selected chemical solution, exposing the outer exterior surfaces of the test specimens to the chemical for the desired length of time.

In some embodiments, the assembly of the specimen-jig-saturated-nonwoven-material may be placed in a bag and sealed to avoid evaporation. In some embodiments, this bag may be made of polyethylene plastic. In some embodiments, the bag may be chosen in such a way which minimizes free volume without contacting the specimen-jig-saturated-nonwoven assembly. In some embodiments with high strain conditions, the specimens may remain in the bag for the requisite 24-hour period 120. In some embodiments with low strain conditions, the specimens may remain in the bag for consecutive 24-hour intervals until the entire seven-day period is achieved 220. In some embodiments, after each 24-hour interval has elapsed the saturated nonwoven material may be replaced with freshly saturated nonwoven material. The bag may also be replaced after every 24-hour interval or sooner if the bag integrity is compromised.

In some methods, the non-woven material may be cut into 2 inch by 2 inch (nominal) squares and wrapped around the entire length of the specimens. In some embodiments, the wrapped nonwoven material may be wrapped with parafilm. In these embodiments, the parafilm may be replaced at 24-hour intervals.

Upon completion of the desired exposure time, the nonwoven material saturated with the chemical is removed from the specimens. The specimen-jig-saturated-nonwoven assembly may be removed from the polyethylene plastic bag. The test specimens (both saturated and control) should be removed from the strain jig(s) 300 being careful not to apply undue load on the specimens. Residual chemicals may be wiped from the test specimens using a clean non-woven patch such that no visible sheen is apparent. The specimens may then be set on a flat surface and allowed a minimum relaxation time of about one hour.

Referring to steps 130 and 230 of FIGS. 1 and 2, after the specimens have received a given relaxation time, they may then be tested using a tensile and/or pendulum (impact) apparatus. In embodiments of the invention, for tensile property tests, the test specimen may be characterized following the ASTM D 638 standard. In some embodiments, impact properties may be evaluated according to a modified unnotched impact testing methodology (Reference ASTM D 6110).

Figure 4B:
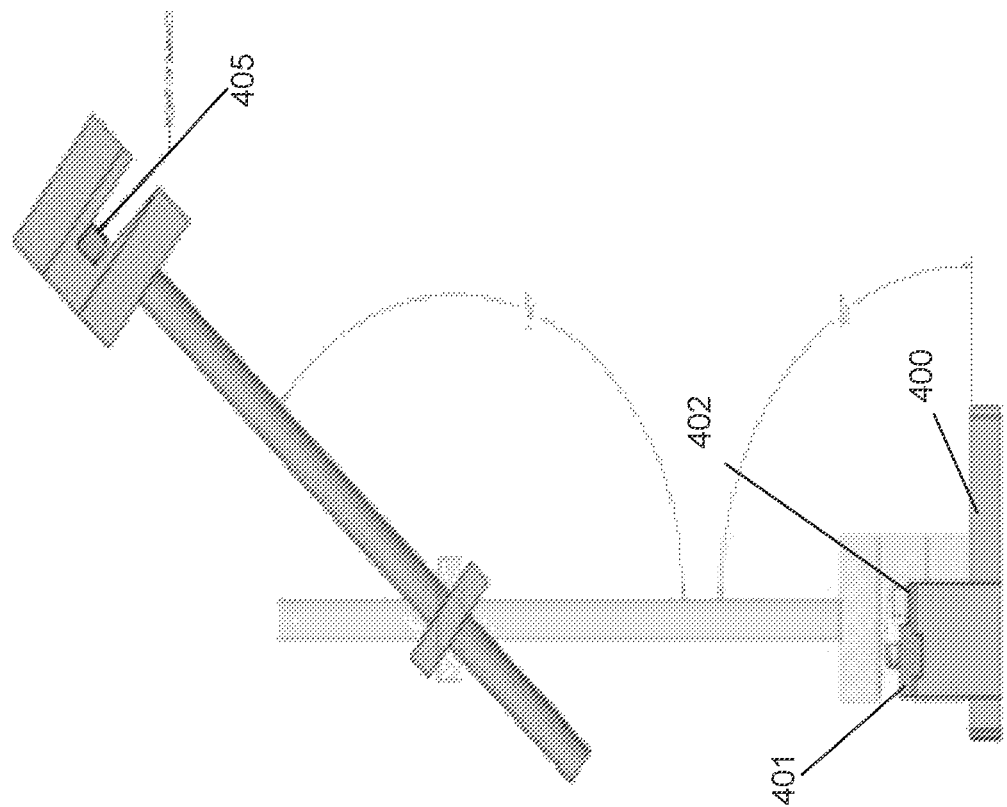
FIG. 4B is a side view of a simple beam impact machine of an embodiment of the invention in a pre-strike position, and a shaded view in post-strike position.
Figure 4A:
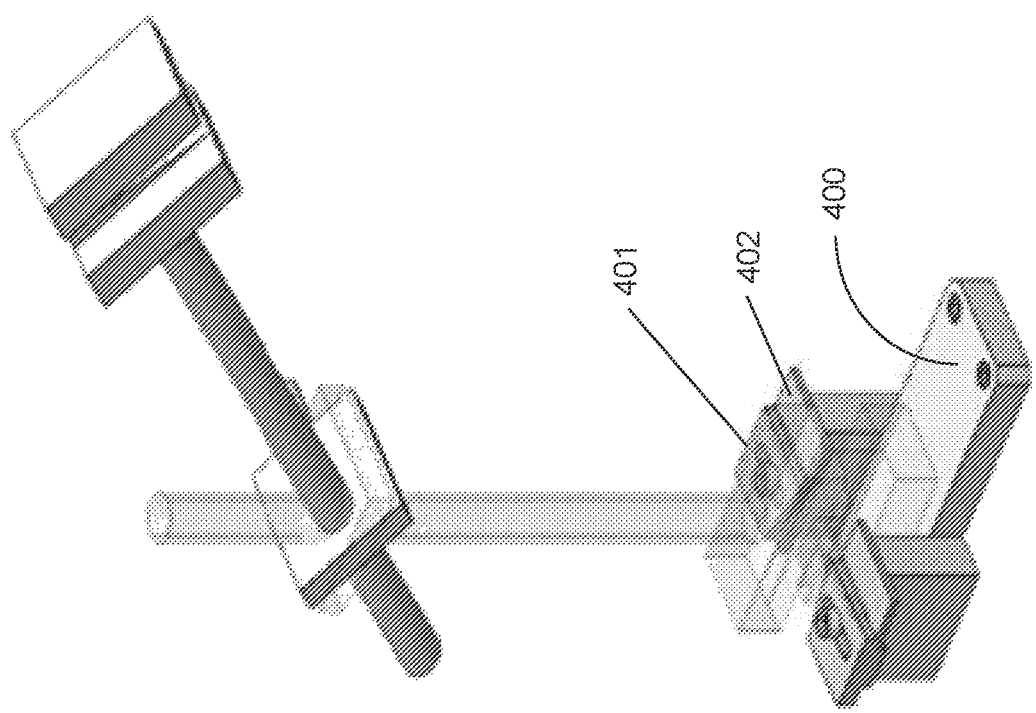
FIG. 4A is a perspective view of a simple beam impact machine of an embodiment of the invention in a pre-strike position, and a shaded view in post-strike position.
Figure 5:
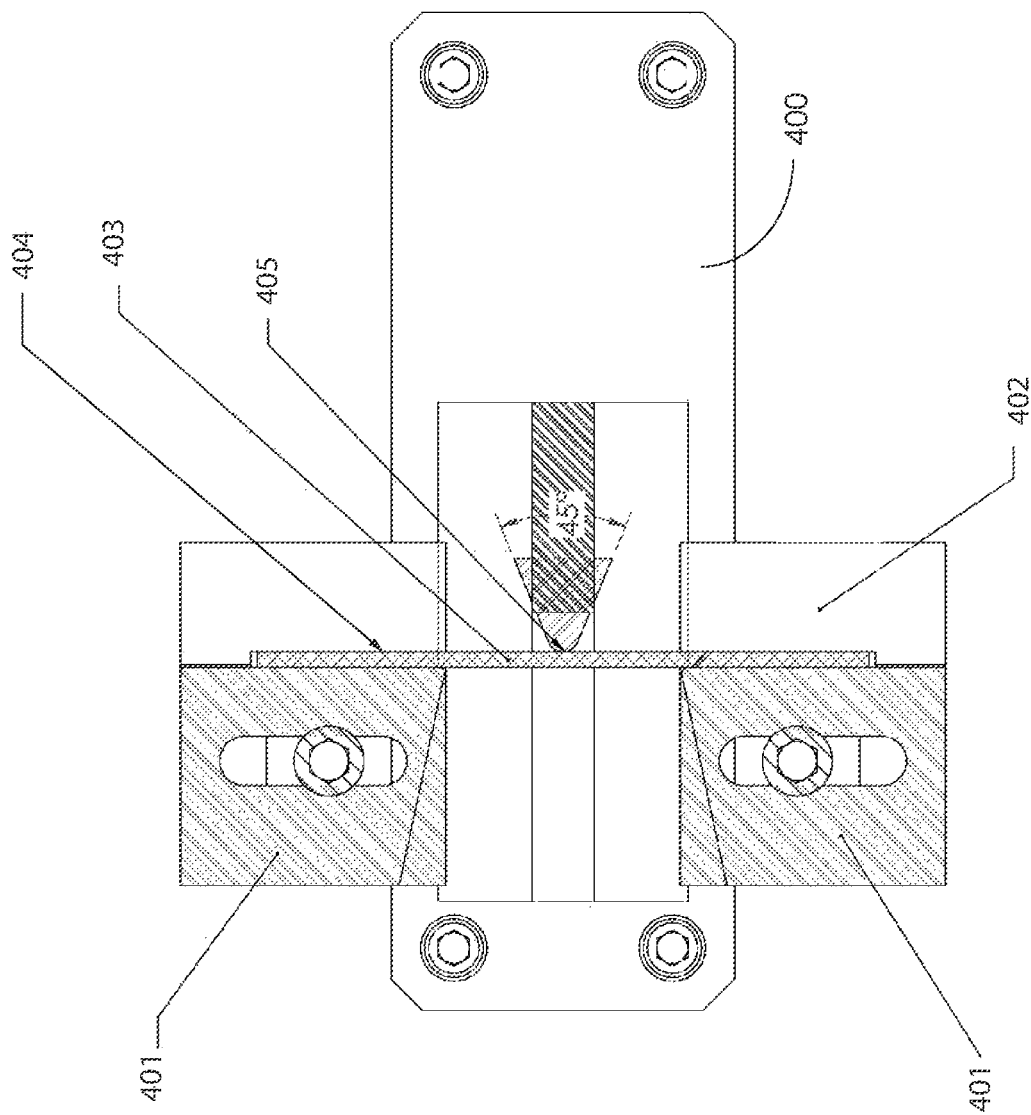
FIG. 5 is a top sectional view of a base of the simple beam impact machine shown in FIGS. 4A and 4B.
Figure 6:
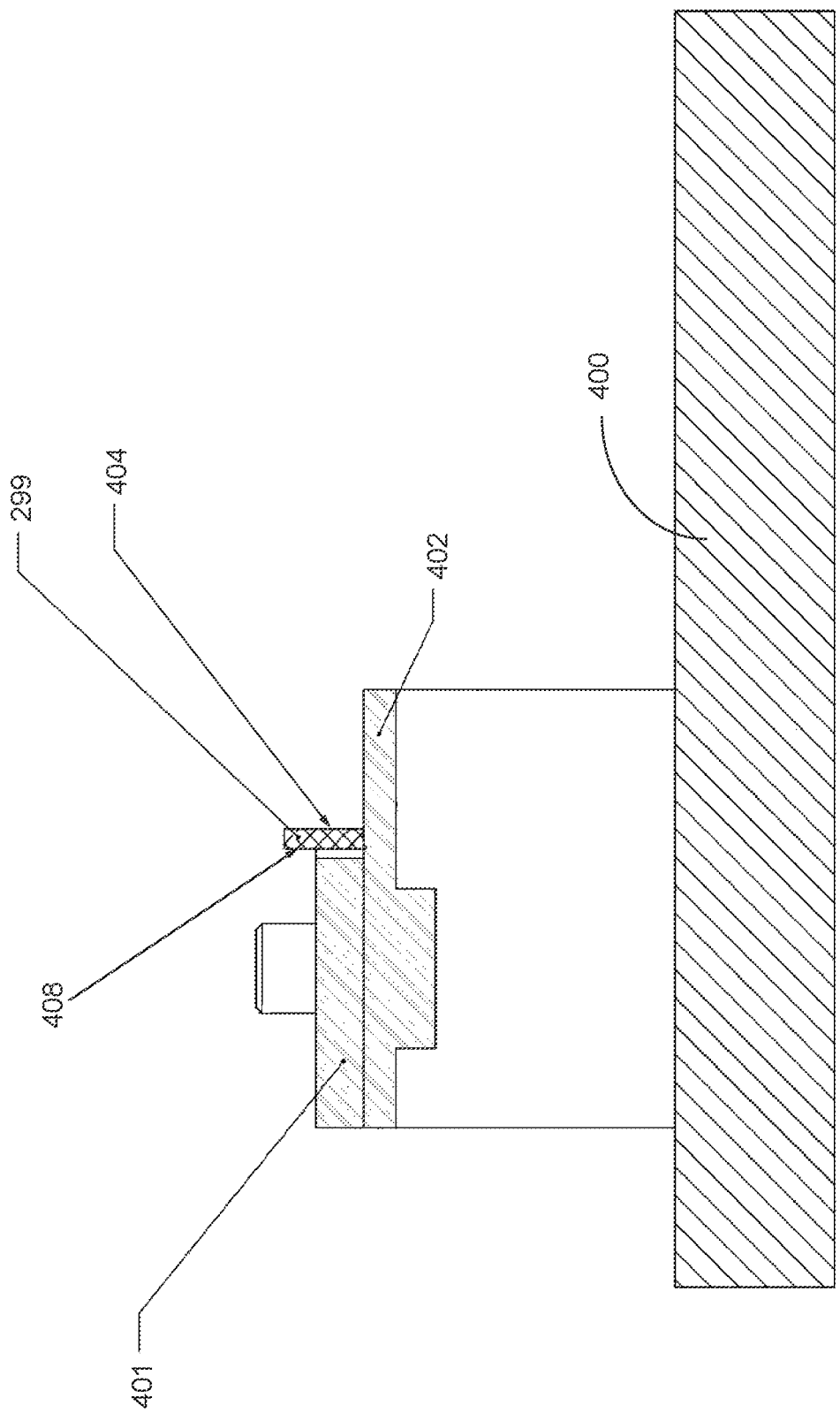
FIG. 6 is a side sectional view of a base of the simple beam impact machine shown in FIGS. 4A and 4B.

Referring to FIGS. 4, 5 and 6, the impact test specimens should be placed vertically in front of Anvil sections 401 and on top of supports 402, with the specimen 299 having an orientation that is perpendicular to the plane defined by base 400 of the platform support. In the exemplary embodiment illustrated in FIGS. 5 and 6, the test specimen has a generally rectangular shape defining a plane, with a longitudinal length that is greater than its lateral height. One surface 408 of the specimen has been exposed to the chemicals, and the other surface 404 has not. The specimen also has a thickness 403, which is ⅛" (0.125 in) in the illustrated example, giving it longer longitudinal edges (along the top and bottom) and shorter lateral edges (left and right sides). Placing the specimen vertically on supports 402 in front of anvil sections 401 means that a longer longitudinal edge (bottom) of the specimen is placed on supports 402 of base 400 such that the plane of the specimen has an orientation that is perpendicular to the plane of the base 400. In these embodiments, for impact testing, the specimen (flex bar) should be centered on the specimen platform support, with the non-chemical exposed side of the specimen 404 facing the hammer 405. Once the specimen is in this unique position, the test should be performed according to ASTM D 6110 standard, releasing hammer 405 so that it strikes the non-exposed side 404 of the specimen 299 as shown in FIG. 5, and the impact energy shown on the display should be recorded. This test should be repeated for each specimen that has been exposed to the chemicals, as well for as each specimen from the control group, with all results recorded. The average results of the tests on the exposed specimens and the tests on the control specimens should then be compared 140, 240.

According to some methods, the user may calculate the percent retention of mechanical properties by taking the quotient of the mean of the test specimens and the mean of the control specimens. In some embodiments, the mechanical properties to be used may be either stress at yield for tensile tests or impact energy for impact tests. This may be determined utilizing the following equations:

Tensile Percent Retention =

$$100 \times \left( \frac{\text{average stress at yield for exposed specimens}}{\text{average stress at yield for unexposed specimens}} \right)$$

Impact Percent Retention =

$$100 \times \left( \frac{\text{average impact energy for exposed specimens}}{\text{average impact energy for unexposed specimens}} \right)$$

In some embodiments, test specimens may be conditioned at 23±2° C. [73±3.6° F.] and 50±10% relative humidity for not less than about 24 hours prior to placement on strain jig in accordance with Procedure A of Practice D 618. In some embodiments shorter time may be sufficient to reach equilibrium. In some embodiments, a tensile retention of >90% may considered to be an effective passing of this method 150, 250. In some embodiments, an impact retention of >90% is considered passing in this method. In some embodiments, lower thresholds may be allowable depending on intended usage of materials.

Set forth below list of standard solutions is intended to be representative of the main categories of chemical species common to healthcare grade disinfectants. All solutions should be made with distilled water. Specific concentrations are on a weight percent basis. Mixing instructions are based on amounts of ingredients calculated to produce 1000 mL of solution of the specified concentration.

The following list of standard solutions is not intended to preclude the use of other reagents pertinent to particular chemical resistance requirements. It is intended to standardize typical industrial products for general testing of the resistance of plastics to common healthcare grade disinfectants.

Standard Reagents

Quaternary Ammonium Compound Solution 1—Add 8 mL of quaternary ammonium compound and 600 mL of isopropyl alcohol to 392 mL of water.

Quaternary Ammonium Compound Solution 2—Add 20 mL of quaternary ammonium compound and 100 mL of diethylene glycol butyl ether to 880 mL of water.

Bleach Solution—Add 20 mL of sodium hypochlorite to 980 mL of water.

Hydrogen Peroxide Solution 1—Add 50 mL of hydrogen peroxide and 50 mL of benzyl alcohol to 900 mL of water.

Hydrogen Peroxide Solution 2—Add 50 mL of hydrogen peroxide and 100 mL of acetic acid to 850 mL of water.

TABLE 3

| Solution Number | Disinfectant Representative | Chemical Species | Weight % |
|---|---|---|---|
| 1 | QACs | Quaternary ammonium compound | .8 |
|   |   | Isopropyl alcohol | 60 |
| 2 | QACS | Quaternary ammonium compound | 2 |
|   |   | Diethylene glycol butyl ether | 10 |
| 3 | Bleach | Sodium Hypochlorite | 2 |
| 4 | Hydrogen Peroxide | Hydrogen Peroxide | 5 |
|   |   | Benzyl alcohol | 5 |
| 5 | Hydrogen Peroxide | Hydrogen Peroxide | 5 |
|   |   | Acetic Acid | 10 |
| 6 | Stand-alone solutions | Isopropyl alcohol | 70 |
| 7 | Stand-alone solutions | Diethylene glycol butyl ether | 10 |
| 8 | Stand-alone solutions | 2-butoxyethanol | 5 |
| 9 | Stand-alone solutions | Hexylene glycol | 30 |

TABLE 3-continued

| Solution Disinfectant Number | Representative Chemical Species | Weight % |
|---|---|---|
| 10 | Top QACs disinfectant by volume sold | 5 |
| 11 | Top Bleach by volume sold | |
| 12 | Top Hydrogen peroxide by volume sold | |

It is to be understood that variations, modifications, and permutations of embodiments of the present invention, and uses thereof, may be made without departing from the scope of the invention. It is also to be understood that the present invention is not limited by the specific embodiments, descriptions, or illustrations or combinations of either components or steps disclosed herein, and that different combinations of the features of the illustrated embodiments may be used in other embodiments, all within the scope of the invention. The illustrated embodiments were chosen and described in order to best explain the principles of the invention and its practical application, to thereby enable others skilled in the art to best utilize the invention and various embodiments with various modifications as are suited to the particular use contemplated. Although reference has been made to the accompanying figures, it is to be appreciated that these figures are exemplary and are not meant to limit the scope of the invention. It is intended that the scope of the invention be defined by the claims appended hereto and their equivalents.

No Warranties

The preceding detailed description has been prepared to solely comply with the provisions of 35 U.S.C. § 112, and does not constitute a commercial warranty, (either expressed or implied), as to the effectiveness of the methods disclosed herein, nor does this disclosure constitute any type of certification or guarantee of any particular outcomes. Therefore, this disclosure may not be relied upon to support any future legal claims including, but not limited to, breach of warranty of merchantability, or fitness for any particular purpose which is directed, in whole, or in part, to the present methods.

What is claimed is:

1. A method of testing a thermoplastic material for compatibility with a chemical comprising the steps of:
    a. selecting a thermoplastic material to be tested;
    b. selecting a chemical for testing with the selected thermoplastic material;
    c. determining a modulus of the thermoplastic material;
    d. selecting a geometry for specimens of the thermoplastic material including a thickness;
    e. selecting a jig having a radius of curvature based on the thickness of the specimens and a strain based on the modulus of the thermoplastic material;
    f. placing a plurality of test specimens of the thermoplastic material on the jig;
    g. placing a plurality of control specimens of the thermoplastic material on the jig;
    h. exposing outer surfaces of the test specimens to the selected chemical for a first predetermined period of time, but not exposing the control specimens to the chemical;
    i. removing both the test specimens and the control specimens from the jig, and waiting for a second predetermined period of time;
    j. testing each of the test specimens for impact according to ASTM D 6110 with the modification of placing the specimen upon an impact pendulum such that a plane defined by the specimen has an orientation that is perpendicular to a plane defined by a base of the pendulum with the exposed outer surface of the specimen facing away from a pendulum head, then striking the specimen with the pendulum head to obtain an impact result, and then recording the impact result;
    k. testing each of the control specimens for impact according to ASTM D 6110 with the modification of placing the specimen upon an impact pendulum such that a plane defined by the specimen has an orientation that is perpendicular to a plane defined by a base of the pendulum before striking the specimen with the pendulum head to obtain an impact result, and then recording the impact result;
    l. averaging the impact results of the test specimens;
    m. averaging the impact results of the control specimens; and
    n. comparing the average test impact results with the average control impact results.

2. The method of claim 1 wherein the selected geometry for the specimens is according to the dimensions defined for ASTM D 638 Type 1 tensile bars.

3. The method of claim 1 wherein the plurality of test specimens comprises at least five specimens, and the plurality of control specimens comprises at least five specimens.

4. The method of claim 1 wherein the first predetermined period of time is about 24 hours.

5. The method of claim 1 wherein the first predetermined period of time is about seven days.

6. The method of claim 1 wherein the second predetermined period of time is about one hour.

7. The method of claim 1 wherein the radius of curvature for the jig is based on the following formula where "t" is the thickness of the material, "Σ" is the strain, and "R" is the radius:

$$R = \frac{\left(\frac{1}{\Sigma} - 1\right)t}{2}.$$

8. The method of claim 7 wherein the testing for tensile properties is according to ASTM D 638.

9. The method of claim 1 comprising the additional steps of, after waiting the second period of time:
    n. testing each test specimen for tensile properties and recording the tensile results;
    o. testing each control specimen for tensile properties and recording the tensile results;
    p. averaging the tensile results of the test specimens;
    q. averaging the tensile results of the control specimens; and
    r. comparing the average test tensile results with the average control tensile results.

10. A method of testing a thermoplastic material for compatibility with a chemical comprising the steps of:
    a. selecting a thermoplastic material to be tested;
    b. selecting a chemical for testing with the selected thermoplastic material;
    c. determining a modulus of the thermoplastic material;
    d. selecting a geometry for specimens of the thermoplastic material that includes a thickness;

e. selecting a jig having a radius of curvature based on the thickness of the specimens and a strain based on the modulus of the thermoplastic material;
f. placing a plurality of test specimens of the thermoplastic material on the jig;
g. placing a plurality of control specimens of the thermoplastic material on the jig;
h. exposing outer surface of the test specimens to the selected chemical for a first predetermined period of time, but not exposing the control specimens to the chemical;
i. removing both the test specimens and the control specimens from the jig, and waiting for a second predetermined period of time;
j. testing each test specimen for tensile properties and recording the tensile results;
k. testing each control specimen for tensile properties and recording the tensile results;
l. averaging the tensile results of the test specimens;
m. averaging the tensile results of the control specimens; and
n. comparing the average test tensile results with the average control tensile results.

11. The method of claim 10 wherein the testing for tensile properties is according to ASTM D 638.

12. The method of claim 10 wherein the selected geometry for the specimens is according to the dimensions defined for ASTM D 638 Type 1 tensile bars.

13. The method of claim 10 wherein the plurality of test specimens comprises at least five specimens, and the plurality of control specimens comprises at least five specimens.

14. The method of claim 10 wherein the first predetermined period of time is about 24 hours.

15. The method of claim 10 wherein the first predetermined period of time is about seven days.

16. The method of claim 10 wherein the second predetermined period of time is about one hour.

17. The method of claim 10 wherein the radius of curvature for the jig is based on the following formula where "t" is the thickness of the material, "Σ" is the strain, and "R" is the radius:

$$R = \frac{\left(\frac{1}{\Sigma} - 1\right)t}{2}.$$

18. The method of claim 10 comprising the additional steps of, after waiting the second period of time:
o. testing each of the test specimens for impact according to ASTM D 6110 with the modification of placing the specimen upon an impact pendulum such that a plane defined by the specimen has an orientation that is perpendicular to a plane defined by a base of the pendulum with the exposed outer surface of the specimen facing away from a pendulum head, then striking the specimen with the pendulum head to obtain an impact result, and then recording the impact result;
p. testing each of the control specimens for impact according to ASTM D 6110 with the modification of placing the specimen upon an impact pendulum such that a plane defined by the specimen has an orientation that is perpendicular to a plane defined by a base of the pendulum before striking the specimen with the pendulum head to obtain an impact result, and then recording the impact result;
q. averaging the impact results of the test specimens;
r. averaging the impact results of the control specimens; and
s. comparing the average test tensile results with the average control tensile results.

* * * * *